United States Patent [19]

Martens et al.

[11] Patent Number: 4,532,796
[45] Date of Patent: Aug. 6, 1985

[54] DUAL TRANSDUCER CONNECTION BY A SINGLE CABLE

[75] Inventors: George D. Martens, New Milford; Alexander B. Smith, Milford; Thomas D. Healy, Norwalk, all of Conn.

[73] Assignee: Automation Industries, Inc., Greenwich, Conn.

[21] Appl. No.: 548,939

[22] Filed: Nov. 7, 1983

[51] Int. Cl.³ .............................................. G01N 29/04
[52] U.S. Cl. ......................................... 73/632; 73/628
[58] Field of Search .................. 73/632, 628, 644, 588

[56] References Cited

U.S. PATENT DOCUMENTS 4,437,332  3/1984  Pittaro .................................... 73/644

Primary Examiner—Anthony V. Ciarlante
Attorney, Agent, or Firm—Francis N. Carten

[57] ABSTRACT

A system for testing the fabrication of objects utilizes echo-sounding techniques. A transmit transducer and a receive transducer which provide a conversion between electric and sonic energies are acoustically coupled to the object under test. A single cable connects the transducers to a single processor which generates, receives and analyzes the signals utilized in the test process. A coupling circuit connects one end of the single cable to the two transducers and isolates a transmitted signal from a received signal so as to permit their communication by the single cable. Within the coupling circuit, a transmitted signal is communicated by a set of serially connected diodes wherein the forward voltage drop is much less than the voltage of the transmitted signal, but greater than the voltage of an incoming signal such as a reverberation of the transmitted signal or a received echo signal. The second channel of the coupling circuit provides for a series connection of a resistor with a set of parallel diodes connected with opposed polarity, the diodes being connected across the terminals of the receive transducer.

3 Claims, 1 Drawing Figure

DUAL TRANSDUCER CONNECTION BY A SINGLE CABLE

BACKGROUND OF THE INVENTION

This invention relates to transducers for the transmission and reception of sonic energy and, more particularly, to a circuit permitting the connections of transmitting and receiving transducers by a single cable to a signal processing apparatus.

Transducers are utilized for the conversion of electrical signals to sonic energy, and the conversion of sonic energy back to electrical signals. While transducers are utilized in a wide variety of situations, one situation of particular interest involves the transmission and reception of sonic signals at very short range. Such a situation arises in the examination of objects, such as a metal pipe, to insure that such objects are properly constructed and free of any defects. For example, in the case of welded pipe, it is advantageous to check the pipe to insure that the weld is properly formed throughout the length of the pipe.

Considering the foregoing situation of the examination of an object, suitable test equipment for accomplishing such examination may be formed in the configuration of a radar system wherein a transmitting transducer and a receiving transducer are acoustically coupled to the exterior of the pipe. The transmitting transducer transmits a sonic wave into the metal pipe which reflects off of the weld and returns by the receiving transducer to a signal processor of the test equipment. In order to provide for good acoustic coupling between the transducers and the pipe, a pair of blocks of acoustic impedance-matching material such as Lucite blocks are advantageously positioned between the radiating surfaces of the transducers and the outer wall of the pipe. The blocks are shaped so as to mate with a wall of the pipe. Specifically, a short pulse signal is transmitted to the pipe. In order to attenuate any acoustic coupling between the two Lucite blocks, a sheet of sound-absorbing cork is disposed between the two blocks. The layer of cork enhances the quality of the received signal by reducing the coupling of any transmitted signal into the path of the received signal.

A problem arises in the use of such test equipment in that the round trip propagation time may be very much shorter than the duration of the test signal. Thus, a portion of the signal reflected from the weld may be received while a latter portion of the test signal is still being transmitted. As a result, two separate signal channels would normally be required for operation with the two transducers since temporal gating circuitry could not be employed in view of the simultaneous presence of the transmit and receive signals at the two transducers. However, in many tests situations, wherein numerous pairs of such transducers may be utilized in a test procedure, it is most desirable to simplify the equipment by employing a single cable for connection between the signal processor and the pair of transducers. However, such a single-cable arrangement is contraindicated in view of the foregoing necessity for two separate signal channels.

SUMMARY OF THE INVENTION

The aforementioned problem is overcome and advantages are provided by a circuit incorporating the invention for connecting a transmit transducer and a receive transducer by a single cable to a signal processor. A coupling circuit of the invention permits the two transducers to be operating in a side by side configuration in a situation, such as the foregoing pipe testing situation, wherein a signal will be simultaneously transmitted and received. The circuit provides for the separation of the transmit and receive signals so that, with reference to the foregoing test situation, any reverberations appearing in the transmit Lucite block are significantly suppressed from entry into the path of the received signal. Thereby, a received signal of high fidelity can be provided for the foregoing test situation.

In accordance with the invention, the circuit includes a series arrangement of diodes connecting with the transmit transducer, and the pair of oppositely-poled paralleled diodes connected in the path of the received transducer. This arrangement prevents the crossover of transmit and received signals between their respective channels so that the single cable can be utilized for the coupling of the signals between the test site and the signal processor.

BRIEF DESCRIPTION OF THE DRAWING

The foregoing aspects and other features of the invention are explained in the following description, taken in connection with the accompanying drawing wherein the sole FIGURE shows a schematic diagram of the coupling circuit of the invention along with the transducers, a pipe under test, and the connection of the transducers via the coupling circuit and a single cable to a signal processor.

DETAILED DESCRIPTION

Figure 1:
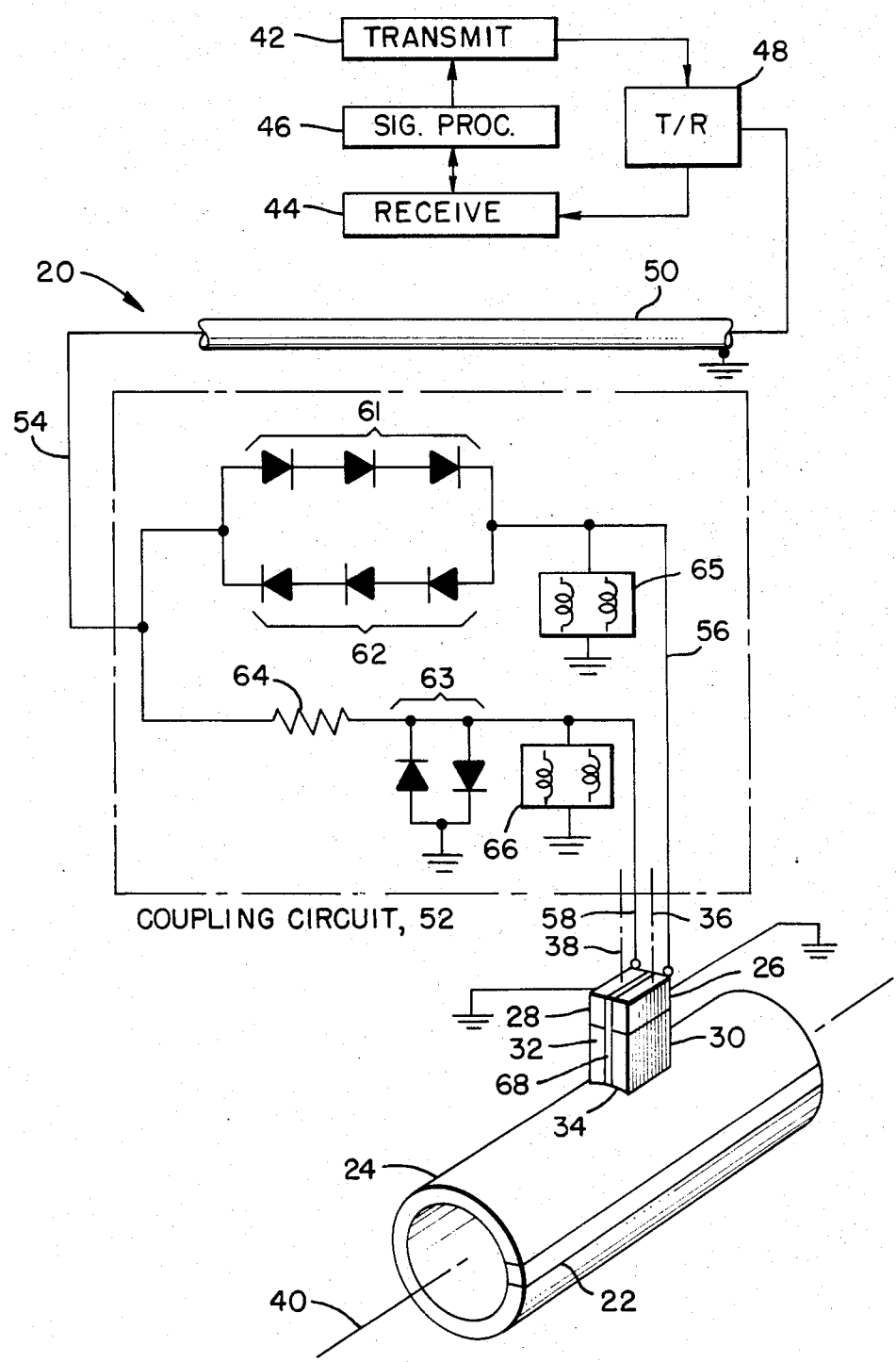

With reference to the sole FIGURE, there is shown a test system 20 utilized for examination of a weld 22 in a pipe 24. By way of example, the pipe 24 may be fabricated of steel. Inspection of the weld 22 is accomplished by use of sonic energy provided by a piezoelectric ceramic transducer 26 which transmits the sound towards the pipe 24. A similarly constructed transducer 28 receives sonic energy which is reflected back from the weld 22. Blocks 30 and 32 abut the radiating surfaces of the transducers 26 and 28, and are also contiguous to the pipe 24 at a meeting surface 34 wherein the blocks 30 and 32 are provided with curved end faces which conform to the shape of the outer surface of the pipe 24. Thereby, the blocks 30 and 32 serve as acoustic transmission paths for the coupling of sonic energy between the pipe 24 and the transducers 26 and 28.

The blocks 30 and 32 serve as impedance matching structures for minimizing the amount of reflection at the interfaces between the block 30 the transducer 26 and the pipe 24, and between the interfaces of the block 32 with the pipe 24 and the transducer 28. The blocks 30 and 32 are fabricated of an acoustically transmissive material, such as Lucite, having a speed of propagation of sound which is slower than the corresponding speed of propagation in the pipe 24. The longitudinal axes 36 and 38 of the blocks 30 and 32 are angled slightly relative to a normal to the surface of the pipe 24, and may also be angled slightly relative to the longitudinal axis 40 of the pipe 24 so as to provide a bending of sound waves at the meeting surface 34. By virtue of the bending of the acoustic waves, the sound waves enter the pipe 24 in a direction oblique to the normal to the surface of the pipe 24 and, therefore, continue to propagate through the pipe 24 to reflect upon the weld 22. The nature of the reflection of the sound waves from the weld 22 provides information as to the quality of the weld 22.

The system 20 further comprises a transmitter 42 and a receiver 44 which are coupled to a signal processor 46, the processor 46 incorporating well known circuitry (not shown) for the generation of an electrical signal which is applied to the transmitter 42 and which analyzes signals received by the receiver 44. The processor 46 also includes well known means (not shown) for timing the respective signals and for displaying the results of the analysis. The output terminal of the transmitter 42 and the input terminal of the receiver 44 are connected by a well known transmit receive circuitry 48 to a single cable 50 which serve as the sole electrical connections between the transmitter 42 and the transmitting transducer 26, and between the receiver 44 and the receiving transducer 28. The cable 50 provides for two-way transmission of electrical signals between the circuitry 48 and the transducers 26 and 28.

In accordance with the invention, the two-way communication of electrical signals between the cable 50 and the transducers 26 and 28 is accomplished by means of a coupling circuit 52. An input line 54 to the circuit 52 connects with the center conductor of the cable 50, there being a ground connection between the circuit 52 and the outer conductor of the cable 50. An output line 56 connects the circuit 52 with the transmitting transducer 26, and a second input line 58 connects the circuit 52 with the receive transducer 28. The circuit 52 comprises two sets 61–62 of serially connected diodes, a set 63 of oppositely poled diodes connected in parallel, and a resistor 64. Also included in the circuit 52 are tuning units 65 and 66.

In operation, the two sets 61–62 of diodes are connected in series with the output transmission line 56. The set 63 of diodes is connected in parallel with the receive transducer 28, the set 63 of diodes being connected between the input receive line 58 and ground. With respect to transmitted signals, the forward voltage drop presented by either set 61 or 62 of the diodes is negligibly small compared to the voltage of the transmitted signal and, accordingly, the set 61–62 may be regarded as being absent with respect to the transmission of the signal on line 56. However, with respect to a signal traveling in the reverse direction along the line 56, such signal resulting from reflections at the end of the block 30 and reverberations therein, it is noted that such a signal would be of substantially reduced voltage, less than the forward voltage drop of the sets 61–62 of the diodes. In this connection, it is noted that each of the transducers 26 and 28 operate to convert electrical energy to sonic energy and vice versa. Each transducer 26 and 28 has properties both of a transmit transducer and a receive transducer. Thus, even though a transmitted signal propagates along the line 56 from the coupling circuit 52 to the transmit transducer 26, a signal propagating in the opposite direction develops as a result of the foregoing acoustic reverberations and reflections associated with the block 30.

In order to insure that there is no more than an insignificant amount of coupling of sonic energy between the two blocks 30 and 32, a layer of sound absorbing material such as cork 68 is placed between the two two blocks 30 and 32. Thereby, the relatively strong acoustic waves within the transmit block 30 are prevented from coupling into the receive block 32. Thereby, the signal received at the block 32 may be regarded as being free of interference from the signal within the transmit block 30.

The received signal traveling along the line 58 presents a voltage which is less than the forward voltage drop of the set 63 of diodes during a state of conduction of either one of the diodes. Accordingly, the set 63 of diodes appears as substantially an open circuit and, therefore, presents no more than a negligible affect upon the received signal. With respect to any tendency of the transmit signal to pass from the line 54 via the resistor 64 to the line 58, the voltage of the transmit signal is much larger than the forward voltage drop across any one of the diodes of the set 63 and, accordingly, substantially all of the voltage of the transmit signal appears as a voltage drop across the resistor 64 so that no more than a negligible amount of transmit signal enters the pipe 24 via the received transducer 28. With respect to received signals traveling along the line 58, the resistance of the resistor 64 is sufficiently small, as compared to other values of resistance presented along the path toward the receiver 44, so as to present no more than a negligible affect to the received signal. Thereby, the resistor 64 with the set 63 of diodes serves to impede the coupling of the transmit signal to the receive transducer 28 while permitting the propagation of a received signal from the transducer 28 to the receiver 44. In this way, the transmit and receive branches of the coupling circuit 52 serve to permit propagation of the transmitted and received signals respectively along the lines 56 and 58 while preventing the passage of the received and transmitted signals, respectively, along the lines 56 and 58.

The transmission and reception of signals by the transducers 26 and 28 can be enhanced by the use of the tuning networks 65 and 66, respectively. For example, the tuning units 65 and 66 may comprise a well-known tuning coil coupled in parallel across the input terminals of the respective ones of the transducers 26 and 28. Also, if desired, the tuning units 65 and 66 may comprise a resistor connected in parallel with respective ones of the transducers 26 and 28 to widen the bandwidth for better reception of a narrow pulse signal. It is also noted that one of the sets 61 or 62 of the diodes may be eliminated if the transmitted signal is of a single polarity, the two sets 61–62 providing for the coupling of both unipolar and bipolar signals, including sinusoidal signals. In the case of a unipolar signal, elimination of one of the sets 61 or 62, in accordance with the polarity of the signal, is advantageous in that the capacitance presented by the diodes is halved, this being advantageous in reducing further any coupling of reverberant signals from the transmit transducer 26. Thereby, the invention permits the use of two transducers, one for transmit and one for receive, with the two transducers being connected by a single cable to a single processor.

It is to be understood that the above-described embodiment of the invention is illustrative only and that modifications thereof may occur to those skilled in the art. Accordingly, this invention is not to be regarded as limited to the embodiment disclosed herein, but is to be limited only by the appended claims.

What is claimed is:

1. A coupling circuit for coupling a relatively large outgoing signal from one terminus of an electrical cable to a first device, and for coupling a relatively small incoming signal from a second device to said cable via said first terminus, said coupling circuit comprising:

a first channel and a second channel, said first channel being connectable between said one terminus and said second device, said second channel being connectable between said first terminus and said second device; and wherein said first channel comprises a set of serially connected diodes being poled for the conduction of current of said outgoing signal towards said first device; and said second channel comprises a set of oppositely poled diodes connected in parallel across terminals of said second device, and a resistor connecting one node of said set of parallel diodes to said one terminal for attenuating any propagation of an outgoing signal in said second channel while said set of serially connected diodes attenuates any incoming signal propagating in said first channel, said outgoing signal having a voltage amplitude larger than the forward voltage drop of said serially connected diodes, the incoming signal from said second device having a voltage amplitude smaller than the forward voltage drop of said parallel connection of diodes.

2. A circuit according to claim 1 wherein said devices are transducers for providing a conversion between electric and sonic energies, said outgoing signal being a transmitted signal and said incoming signal being a received signal or a reverberation of said outgoing signal.

3. A circuit according to claim 2 comprising first and second tuning units disposed, respectively, in said first and second channels for tuning said transducers.

* * * * *